United States Patent [19]

Eiglmeier et al.

[11] 4,446,075
[45] May 1, 1984

[54] SUBSTITUTED BROMOFLUOROBENZENE DERIVATIVES AND PROCESS FOR ITS MANUFACTURE

[75] Inventors: Kurt Eiglmeier, Seelze; Reinhard Knieps, Hanover, both of Fed. Rep. of Germany

[73] Assignee: Riedel-de Haen AG, Seelze, Fed. Rep. of Germany

[21] Appl. No.: 236,546

[22] Filed: Feb. 20, 1981

[30] Foreign Application Priority Data

Feb. 22, 1980 [DE] Fed. Rep. of Germany ....... 3006685

[51] Int. Cl.$^3$ ..................... C07C 120/00; C07C 47/55
[52] U.S. Cl. ........................... 260/465 G; 260/544 D; 562/493; 568/433; 568/938; 570/127; 570/140; 570/141; 570/143; 570/174
[58] Field of Search ............... 570/127, 140, 141, 143, 570/174; 568/433, 938; 260/465 G, 544 D; 562/493

[56] References Cited

U.S. PATENT DOCUMENTS

| | | | |
|---|---|---|---|
| 2,180,772 | 5/1938 | Scherer | 570/127 X |
| 3,371,025 | 2/1968 | Tatlow et al. | 570/174 X |
| 3,689,559 | 9/1972 | Taylor et al. | 568/433 X |
| 4,036,887 | 7/1977 | Sheldon et al. | 568/433 |
| 4,218,567 | 8/1980 | Manchand et al. | 568/433 X |

FOREIGN PATENT DOCUMENTS

| | | | |
|---|---|---|---|
| 2201826 | 7/1973 | Fed. Rep. of Germany | 570/143 |
| 2259870 | 6/1974 | Fed. Rep. of Germany | 570/174 |
| 835727 | 12/1938 | France . | |

OTHER PUBLICATIONS

Recueil des Travaux Chimiques des Pays Bas, vol. 83, 1964, pp. 1142–1148.
Comptes Rendus Hebdomadaires des Seances de l'Academie des Sciences, vol. 263, 1966, pp. 145–148.
The Journal of Organic Chemistry, vol. 21, 1956, pp. 934–938.

*Primary Examiner*—Thomas A. Waltz
*Attorney, Agent, or Firm*—Curtis, Morris & Safford

[57] ABSTRACT

Substituted bromofluorobenzene, wherein the fluorine is in para-position and the bromine in meta-position to another substituent, is prepared by direct bromination of the corresponding fluorobenzene derivative. Bromination is advantageously carried out in the presence of a catalyst, preferably a metal or metal salt. The elementary bromine is used in an amount of 0.9 to 1.3 mols per mol of fluorobenzene derivative and the reaction temperature is between 20° and 200° C. The bromofluorobenzene derivatives are suitable for the synthesis of medicaments and plant protective agents.

6 Claims, No Drawings

SUBSTITUTED BROMOFLUOROBENZENE DERIVATIVES AND PROCESS FOR ITS MANUFACTURE

The invention relates to substituted bromofluorobenzene which can be obtained by direct bromination of substituted fluorobenzene, and a process for its manufacture.

The manufacture of certain 3-bromo-4-fluorobenzene derivatives is known. 3-Bromo-4-fluorobenzoic acid, for example, is obtained by oxidation of 3-bromo-4-fluorotoluene which is prepared by diazotization of 3-bromo-4-aminotoluene and controlled decomposition of the isolated diazonium tetrafluoroborate. 3-Bromo-4-fluoroacetophenone is obtained from 2-fluorobromobenzene which is not readily accessible by reaction with acetyl chloride. In this case, the 2-fluorobromobenzene must be prepared from 2-fluoroaniline (see Rec. Trav. Chim. 83 (1964), 1142). Moreover, 3-bromo-4-fluoronitrobenzene can be obtained from 4-fluoronitrobenzene with the aid of stoichiometric amounts of expensive silver salt (see J. Org. Chem. 21 (1956) 934).

An object of the invention is the preparation of substituted bromofluorobenzene which can be obtained in a technically simple way from readily accessible starting material.

The invention relates to a substituted bromofluorobenzene of the formula (1)

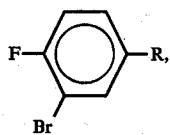

(1)

wherein R means a carboxy, halocarboxy, nitro, cyano or COR¹ group, with R¹ being a hydrogen atom or a lower alkyl or aryl group, which can be obtained by direct bromination of a substituted fluorobenzene of the formula (2)

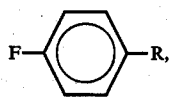

(2)

wherein R has the abovementioned meaning. The halocarboxy group preferably is a chlorocarboxy or bromocarboxy group. The lower alkyl group means an alkyl group with 1 to 6 carbon atoms, preferably 1, 2 or 3 carbon atoms, and the aryl group preferably is a phenyl group which may optionally be substituted by a lower alkyl group.

The invention especially relates to a substituted bromofluorobenzene of formula (3)

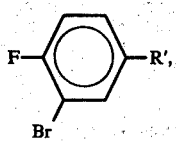

(3)

wherein R' means a cyano, formyl or bromocarboxy group, i.e. 3-bromo-4-fluorobenzonitrile, 3-bromo-4-fluorobenzaldehyde and 3-bromo-4-fluorobenzoyl bromide.

Moreover, the invention relates to a process for the manufacture of a substituted bromofluorobenzene, which comprises subjecting a substituted fluorobenzene of the formula (2)

wherein R means a carboxy, halocarboxy, nitro, cyano or COR¹ group, with R¹ being a hydrogen atom or a lower alkyl or aryl group, to direct bromination.

As starting material for the process according to the invention, 4-fluorobenzoyl chloride, 4-fluorobenzoyl bromide, 4-fluoro-benzaldehyde, 4-fluoroacetophenone, 4-fluorobenzonitrile, 4-fluoronitrobenzene, 4-fluorobenzoic acid and 4-fluorobenzophenone are especially suitable.

The process according to the invention is advantageously carried out in the presence of a catalyst. Suitable catalysts are especially iodine, metals and metal salts, preferably trivalent metals, for example iron, and halides of trivalent metals, for example iron(III) halides, such as iron(III) chloride and iron(III) bromide as well as aluminum(III) halides such as aluminum(III) chloride and aluminum(III) bromide. The catalyst is used in an amount of 0.02 to 2 mols, preferably 0.02 to 0.3 mol in the case of iodine and metals, and in an amount of 1 to 1.2 mols in the case of metal salts, per mol of fluorobenzene derivative.

When using a metal salt as catalyst, it is recommendable to carry out the process in the presence of an organic solvent, especially an aliphatic halogenated hydrocarbon, preferably a chlorinated hydrocarbon, with 1 or 2 carbon atoms, for example chloroform, methylene chloride, carbon tetrachloride and 1,2-dichloroethane.

An important characteristic of the process according to the invention is the direct bromination of the starting material. For this purpose, elementary bromine is used in an amount of 0.9 to 1.3 mols, preferably 1.0 to 1.2 mols, per mol of fluorobenzene derivative. Advantageously oxidants, preferably chlorine, are added simultaneously, thus oxidating the resulting hydrogen bromide to bromine, which can be reused without difficulty for bromination. The oxidant is optionally used in the same molar amount as the bromine. Thus, the required amount of bromine is reduced to 50% of the amount necessary, without the oxidant.

Bromination is carried out at a temperature of 20° to 200° C. When using a metal as catalyst, the temperature advantageously is from 100° to 170° C., while in the presence of a metal salt as catalyst a temperature of 35° to 60° C. is especially suitable.

For the preparation of 3-bromo-4-fluorobenzaldehyde as substituted bromofluorobenzene the process according to the invention is especially suitable in modified form. This variant consists in reacting 4-fluorotoluene with bromine to give 4-fluorobenzalbromide in a first reaction step, hydrolizing same to 4-fluorobenzaldehyde in a second reaction step and subsequently converting the 4-fluorobenzaldehyde via direct bromination into 3-bromo-4-fluorobenzaldehyde.

This modified process is carried out as one-pot process, since isolation of the intermediate is not necessary. The side chain bromination of the first reaction step is preferably carried out under the action of shortwave light or in the presence of a catalyst. For this purpose radical-forming agents, especially aliphatic azo compounds, for example α, α'-azoisobutyronitrile, azodicarboxylic acid amide, azodicarboxylic acid dialkyl esters such as azodicarboxylic acid diethyl ester, -diisopropyl ester or -ditertiary butyl ester as well as azo-γ, γ'-bis(4-cyanovaleric acid are useful. Hydrolysis of the second reaction step is also carried out preferably in the presence of a catalyst or a base. The catalyst is preferably an acid salt such as zinc chloride, and the base is an inorganic base such as potassium carbonate or calcium carbonate. The bromination of the nucleus in the third reaction step is also preferably carried out in the presence of a catalyst, especially iodine, a metal or a metal salt, as described above.

The processes according to the invention can be carried out in a technically simple and economic way. The bromofluorobenzene derivatives are obtained in a purity degree of more than 95%, preferably 97 to 99.5% (determined by gas chromatography). Halogen isomerization at the aromatic nucleus of the starting material has not been observed.

The 3-bromo-4-fluorobenzene derivatives obtained according to the invention are valuable intermediates, which are especially suitable for the synthesis of pharmaceutical and plant protective agents.

The following examples illustrate the invention. Percentages are percentages by weight.

EXAMPLE 1

0.965 kg (7.24 mols) of aluminum chloride are first introduced into 1.9 kg of 1.2-dichloroethane and then 0.8 kg (5.79 mols) of 4-fluoroacetophenone, in such a manner that the temperature of the mixture does not exceed 45° C. While maintaining the temperature of 45° C., 1.02 kg (6.38 mols) of bromine are added dropwise within 4 hours while stirring, and then stirring of the mixture is continued for 3 hours. Subsequently, the mixture is introduced into a mixture of 5.75 kg of ice and 0.535 kg of hydrochloric acid (37%). After separation of the organic phase and distillation, 1 kg of 3-bromo-4-fluoroacetophenone (78.5% of theory) with a melting range of 53° to 55.5° C., a boiling range of 125° to 126° C. (at a pressure of 20 mbar) and a purity degree of 98.7% is obtained.

EXAMPLE 2

Analogously to Example 1, 3-bromo-4-fluorobenzaldehyde with a melting range of 27° to 29° C., a boiling range of 112° to 115° C. (at a pressure of 25 mbar) and a purity degree of 99.0% is obtained from 4-fluorobenzaldehyde.

EXAMPLE 3

Analogously to Example 1, 3-bromo-4-fluorobenzonitrile with a melting range of 53.8° to 55.5° C., a boiling range of 134° to 136° C. (at a pressure of 44 mbar) and a purity degree of 99.7% is obtained from 4-fluorobenzonitrile.

EXAMPLE 4

3.0 g (0.054 mol) of iron powder are added to 250 g (1.77 mols) of 4-fluoronitrobenzene and the mixture is heated to a temperature of 140° C. During 9 hours, 450 g (2.81 mols) of bromine are added dropwise, while additionally adding portionwise a total of another 15 g (0.27 mol) of iron powder. Subsequently, stirring of the mixture is continued for 6 hours. After filtration, the filtrate is taken up in 530 g of hot n-hexane. After cooling of the solution, 220 g of crystalline 3-bromo-4-fluoronitrobenzene (55.8% of theory) with a melting range of 55.5° to 56.5° C. and a purity degree of 99.0 are obtained.

EXAMPLE 5

Analogously to Example 4, a mixture of 3-bromo-4-fluorobenzoyl chloride and 3-bromo-4-fluorobenzoyl bromide is obtained from 4-fluorobenzoyl chloride. By distillation of this mixture, 3-bromo-4-fluorobenzoyl bromide is isolated in the form of colorless crystals with a melting range of 34.8° to 35.8° C. and a purity degree of 99.3%.

EXAMPLE 6

250 g (2.27 mols) of 4-fluorotoluene are added to 1.25 g (7.61 mmols) of α, α'-azoisobutyronitrile and heated to a temperature of 110° C. In the course of 4 hours, 725 g (4.54 mols) of bromine are added dropwise while raising the temperature of the reaction mixture to 145° C. 1.25 g (9.17 mmols) of zinc chloride are added to the mixture substantially consisting of 4-fluorobenzalbromide, and subsequently 40 g of water are added within 6 hours. After cooling to a temperature of 80° C. and addition of 1,160 g (930 ml) of 1,2-dichloroethane, the mixture is cooled to 150° C. Subsequently, 500 g of aluminum chloride are added portionwise to the mixture without exceeding a temperature of 20° C. Then, the mixture is heated to 40° C., and during 6 hours 382 g (2.39 mols) of bromine are added dropwise; afterwards, stirring of the mixture is continued for 16 hours at a temperature of 40° C. The reaction mixture is slowly poured onto a mixture of 2,400 g of ice and 105 g of concentrated hydrochloric acid, and thoroughly stirred for 5 minutes. The organic phase of the mixture is separated and washed twice with water and 10% aqueous sodium carbonate solution, respectively, and once with water. After evaporation of the 1,2-dichloroethane the product is fractionated. There are obtained 210 g (45%, relative to 4-fluorotoluene) of 3-bromo-4-fluorobenzaldehyde with a boiling range of 92° to 98° C. (at a pressure of 17 mbar) and a purity degree of more than 99%.

What is claimed is:

1. A process for the manufacture of a substituted bromofluorobenzene of the formula

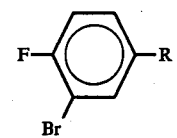

wherein R is a cyano or COR$^1$ group, with R$^1$ being a hydrogen atom or a lower alkyl or an aryl group, which comprises subjecting a substituted fluorobenzene of the formula

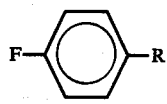

wherein R has the above-mentioned meaning, at a temperature of 20° to 200° C., to direct bromination with bromine in an amount of 0.9 to 1.3 mols per mol of said fluorobenzene in the presence of 0.02 to 0.3 mols of iodine or of 0.02 to 0.3 mols of a trivalent metal or of 1 to 1.2 mols of a halide of a trivalent metal, in each case per mol of said fluorobenzene.

2. The process of claim 1 wherein the bromination is carried out in the presence of a trivalent metal at a temperature of 100° to 170° C.

3. The process of claim 1 wherein the bromination is carried out in the presence of a halide of a trivalent metal at a temperature of 35° to 60° C.

4. The process of claim 1 wherein the bromination is carried out in the presence of chlorine which is used in the same molar amount as the bromine.

5. A process for the manufacture of 3-bromo-4-fluorobenzaldehyde comprising the steps of preparing 4-fluorobenzalbromide by reacting 4-fluorotoluene with bromine, forming 4-fluorobenzaldehyde by hydrolyzing the 4-fluorobenzalbromide and preparing 3-bromo-4-fluorobenzaldehyde by subjecting the 4-fluorobenzaldehyde to direct bromination at a temperature of 20° to 200° C. with bromine in an amount of 0.9 to 1.3 mols per mol of 4-fluorobenzaldehyde in the presence of 0.02 to 0.3 mols of iodine or of 0.02 to 0.3 mols of a trivalent metal or of 1 to 1.2 mols of a halide of a trivalent metal, in each case per mol of 4-fluorobenzaldehyde.

6. The process of claim 5, wherein the process is carried out as a one pot process.

* * * * *